US011090429B2

(12) United States Patent
Colli et al.

(10) Patent No.: US 11,090,429 B2
(45) Date of Patent: Aug. 17, 2021

(54) CANNULA FOR THE PERFUSION OF A FLUID

(71) Applicants: Andrea Colli, Pisa (IT); Paolo Peruzzo, Mirano (IT)

(72) Inventors: Andrea Colli, Pisa (IT); Paolo Peruzzo, Mirano (IT)

(*) Notice: Subject to any disclaimer, the term of this patent is extended or adjusted under 35 U.S.C. 154(b) by 397 days.

(21) Appl. No.: 15/954,952

(22) Filed: Apr. 17, 2018

(65) Prior Publication Data
US 2019/0099553 A1    Apr. 4, 2019

(30) Foreign Application Priority Data
Oct. 3, 2017   (IT) .................... 102017000110730

(51) Int. Cl.
*A61M 5/158*   (2006.01)
*A61M 5/168*   (2006.01)
(Continued)

(52) U.S. Cl.
CPC .......... *A61M 5/158* (2013.01); *A61M 1/3659* (2014.02); *A61M 5/16813* (2013.01);
(Continued)

(58) Field of Classification Search
CPC ............ A61M 1/3659; A61M 5/16813; A61M 25/0068; A61M 25/007; A61M 2025/0003; A61M 2025/0037; A61M 2025/0073
(Continued)

(56) References Cited

U.S. PATENT DOCUMENTS 5,558,652 A * 9/1996 Henke ............... A61M 25/0108
600/435
2007/0287967 A1   12/2007 Hekmat
(Continued)

FOREIGN PATENT DOCUMENTS

WO     1993012826 A1    7/1993

OTHER PUBLICATIONS

International Search Report in PCT/IB2018/057672, dated Jan. 23, 2019.
(Continued)

*Primary Examiner* — Brandy S Lee
*Assistant Examiner* — Nidah M Hussain
(74) *Attorney, Agent, or Firm* — Kristina Castellano; Castellano PLLC

(57) ABSTRACT

Cannula for fluid perfusion comprising a tubular body extending from a proximal portion to a distal portion thereof, the tubular body being provided with an internal cavity defining a first opening in the distal portion allowing a fluid to exit the cavity in a first direction, the tubular body comprising a connection portion lying between the proximal and distal portions, the connection portion being designed to be inserted into a blood vessel by the distal portion. The cannula furthermore comprises a duct extending from a first end to a second end thereof, the second end being provided with an auxiliary opening placed at the connection portion so as to allow a fluid to exit the duct in a second direction opposite to the first direction. The first end is placed in fluid communication with the cavity so that a fluid flowing in the cavity toward the first opening flows at least in part into the duct, said duct being provided with a valve device designed to shut off, or allow, the flow of a fluid flowing through the duct from one end to the other thereof, depending on (Continued)

whether the valve device is in a first configuration or a second configuration, respectively.

10 Claims, 2 Drawing Sheets

(51) Int. Cl.
  *A61M 25/00* (2006.01)
  *A61M 1/36* (2006.01)
(52) U.S. Cl.
  CPC ...... *A61M 25/007* (2013.01); *A61M 25/0028* (2013.01); *A61M 25/0068* (2013.01); *A61M 2025/0003* (2013.01); *A61M 2025/0031* (2013.01); *A61M 2025/0037* (2013.01); *A61M 2025/0073* (2013.01)
(58) Field of Classification Search
  USPC ......................................................... 604/256
  See application file for complete search history.

(56) References Cited

U.S. PATENT DOCUMENTS

| | | | |
|---|---|---|---|
| 2012/0259273 A1* | 10/2012 | Moshinsky | A61M 1/3659 604/28 |
| 2014/0330250 A1 | 11/2014 | Moshinsky | |
| 2015/0126972 A1 | 5/2015 | Ravenscroft | |
| 2016/0121079 A1* | 5/2016 | Walther | A61M 39/22 604/508 |

OTHER PUBLICATIONS

Written Opinion in PCT/IB2018/057672, dated Jan. 23, 2019.
Search Report of the Italian application (dated Apr. 11, 2018).

* cited by examiner

CANNULA FOR THE PERFUSION OF A FLUID

CROSS REFERENCE TO RELATED APPLICATIONS

This application claims priority to Italian patent application 102017000110730 filed on Oct. 3, 2017, the contents of which are incorporated herein by reference.

FIELD

The present invention refers to a cannula for fluid perfusion.

BACKGROUND OF THE INVENTION

The cannula according to the invention can be applied, although not exclusively, in the technical field of providing medical care aimed at administering a fluid, such as an isotonic or hypertonic medicinal solution or blood, to an organ or system of the body through a vein or artery.

An example of a bi-directional perfusion cannula is described in United States patent application US 2014/0330250 A1. This cannula comprises a main tubular element with longitudinal ends that are provided with corresponding openings. An additional hole is made in an elbow section of the main tubular element. The opening made at one longitudinal end of the main tubular element allows a fluid to be supplied to an artery in a first direction, while the hole in the elbow section allows the aforementioned fluid to be injected into the artery in a second direction opposite to the first. The cannula of US 2014/0330250 A1 can include a secondary tube that passes through the main tubular element and terminates at an opening adjacent to the hole in the elbow section. A pressure transducer may be connected to the secondary tube to check for proper initial positioning of the cannula inside the artery.

However, the Applicant has observed that this technical solution is relatively fragile and complex, particularly in the elbow section, as it calls for a plurality of holes in that section in order to inject a fluid into the artery in two opposite directions, and to check for proper positioning of the cannula.

In addition, the technical solution of the cannula described in US 2014/0330250 A1 is not very versatile as it is only suitable for bi-directional perfusion.

BRIEF DESCRIPTION OF SEVERAL VIEWS OF THE DRAWINGS

The features and additional benefits of the invention will become clearer from the following detailed description of a preferred, non-exclusive embodiment, given as a non-limiting example in reference to the appended drawings, in which.

DETAILED DESCRIPTION

Figure 1:
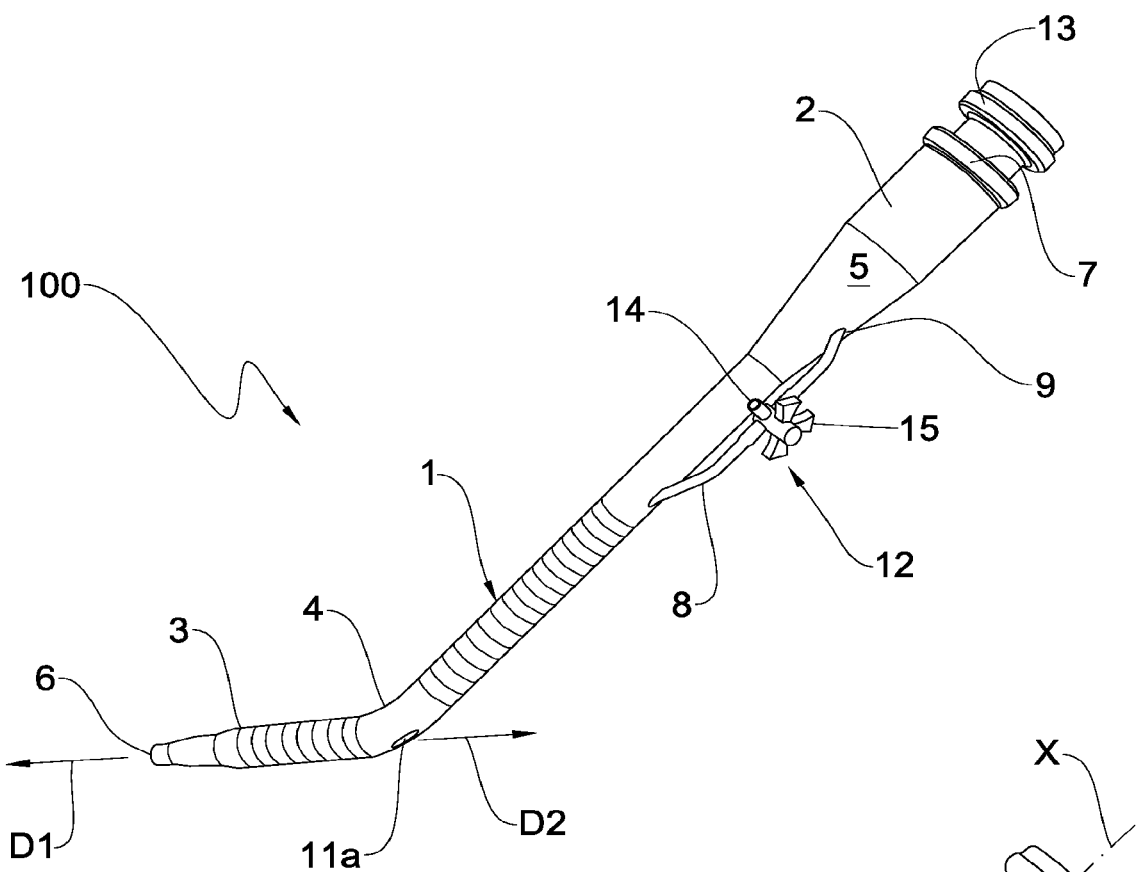
FIG. 1 is a perspective view of a cannula according to the invention.

The purpose of this invention is to provide a cannula for fluid perfusion that overcomes at least one of the drawbacks of the identified prior art.

This purpose is achieved by means of a cannula for fluid perfusion according to the independent claim appended to this description.

The preferred characteristics of the invention are defined in the dependent claims.

According to a feature of the invention, the cannula for fluid perfusion comprises a tubular body extending from its proximal portion to its distal portion.

The distal portion is intended to be inserted into a blood vessel.

In the context of this invention, the fluid perfused through the cannula may be a medicinal or nutritional substance, or a biological fluid (for example, blood).

The tubular body comprises a connection portion lying between the proximal and distal portions. The connection portion is configured, or may be configured, so as to follow a curve and is sized so as to be inserted into a blood vessel through the distal portion.

The inside of the tubular body is provided with a cavity defining a first opening in the distal portion. The first opening allows a fluid to exit the cavity in a first direction.

Preferably, the first direction is substantially the same as the direction of insertion of the distal portion of the cannula into the blood vessel. In particular, the first direction may be the same as the direction of blood flow in the cannulated blood vessel.

According to a feature of the invention, the cannula comprises a duct extending from a first end to a second end thereof.

The first end of the duct is placed in fluid communication with the cavity of the tubular body so that a fluid flowing in said cavity toward the first opening flows at least in part into the duct.

Preferably, a hole made in the tubular body places the first end of the duct in fluid communication with the cavity.

The second end of the duct is provided with an auxiliary opening placed in the connection portion of the tubular body so as to allow a fluid to flow out of the duct in a second direction opposite to the aforementioned first direction.

In particular, the second direction is substantially opposite to the insertion direction of the distal portion in the blood vessel.

According to a feature of the invention, the duct is provided with a valve device designed to shut off, or allow the flow, of a fluid flowing through the duct from one end to the other thereof, depending on whether the valve device is in a first configuration or a second configuration, respectively.

In other words, when in the first configuration the valve device closes the duct and prevents the flow of a fluid from the first to the second end, and vice versa. On the contrary, when in the second configuration the valve device leaves the duct substantially open and allows a fluid to flow from the first end to the second end, and vice versa.

This combination of characteristics allows a user of the cannula, that is, a physician or the nursing staff, to ascertain the proper positioning of the cannula in the blood vessel and allows the user the option of choosing between unidirectional perfusion (that is, introduction of a fluid into the blood vessel through the first opening only, and therefore in the first direction) or bi-directional perfusion (that is, introduction of a fluid into the blood vessel in both the first and second directions simultaneously) as a function of specific medical requirements, as will be described in greater detail below.

In the context of this invention, the condition of proper cannula positioning in the blood vessel is achieved when the auxiliary opening of the duct is placed inside the blood vessel in such a way as to not be obstructed by the inside walls of the blood vessel.

It must be noted that the cannula described in US 2014/0330250 A1 does not provide the option of choosing and setting uni- or bi-directional perfusion, since the cavity extending within the tubular element of that cannula always puts the hole in the elbow section in fluid communication with the opening made in the longitudinal end of the aforementioned tubular element inserted into the blood vessel. In addition, the connection portion of the cannula according to the invention has a simplified structure compared to the elbow section of the cannula in US 2014/0330250 A1.

In particular, the duct of the cannula according to the invention is provided with an intermediate hole placed between the first and second ends of the duct, while the valve device is preferably a three-way valve that can be moved between the first and second configurations. The three-way valve comprises a shutter placed inside the duct and may include a knob by means of which an operator is capable of placing the valve device in the desired configuration by rotating the knob.

According to a feature of the invention, in the first configuration of the valve device the shutter is set to occlude the duct while keeping the intermediate hole substantially open so as to divert a fluid injected into the duct through the auxiliary opening toward the intermediate hole, through which the fluid exits the duct.

In the second configuration of the valve device, the shutter is set to occlude the intermediate hole while keeping the duct substantially open so as to allow a fluid to flow from the first end to the second end, or vice versa.

According to a feature of the invention, a connector can extend from the intermediate hole of the duct. Preferably, the connector is arranged to be connected to an inlet tube of a pressure transducer to measure the pressure of a fluid passing through the aforementioned intermediate hole.

With the valve device in the first configuration, the cannula can be inserted into a blood vessel through the distal portion until the connection portion is placed inside said blood vessel. If the auxiliary opening is placed inside the blood vessel in such a way as to not be obstructed by the inside walls thereof, the blood flowing in the blood vessel is free to enter the duct through the auxiliary opening and therefore to flow toward the second end of the duct.

In particular, the valve device in the first configuration prevents the blood flowing into the duct from entering the cavity of the tubular element through the first portion of the duct and at the same time same allows that blood to pass through the intermediate hole in the duct. This condition makes it possible to ascertain proper positioning of the cannula in the blood vessel.

Conversely, if the cannula is placed in the blood vessel so that the auxiliary opening is located outside the blood vessel, or inside the blood vessel but in a position in which the cannula is obstructed by the inside wall of the blood vessel because it is up against, or near, the blood vessel, blood is prevented from going back into the duct through the auxiliary opening. Consequently, this condition is an indication of incorrect positioning of the cannula in the blood vessel.

Furthermore, the valve device in the first configuration allows for unidirectional perfusion of a fluid into the blood vessel. Indeed, the valve device in this condition obstructs the duct, allowing a fluid present in the cavity of the tubular body the option of exiting only through the first opening in the first direction.

The fact that the intermediate hole is left open by the valve device when in the first configuration furthermore allows for the perfusion of a first fluid into a blood vessel through the first opening in the cannula, as well as the perfusion of a second fluid through the auxiliary opening in the duct, with the second fluid being supplied by a source external to the cannula and injected into the duct through the intermediate hole.

The second configuration of the valve device, however, leaves the duct unobstructed so that the fluid present in the cavity of the tubular body is free to flow in part toward the distal portion, thus exiting the first opening in the first direction, and in part into the duct, thus exiting the auxiliary opening in the second direction. In particular, the valve device in the second configuration occludes the intermediate hole, thus preventing a fluid flowing in the duct from exiting through this hole. This condition allows for bi-directional perfusion of the same fluid in a blood vessel.

According to a feature of the invention, the valve device, particularly in the form of a three-way valve, can assume additional configurations other than the aforementioned first and second configurations, preferably by rotation of the device's knob.

Specifically, the valve device can be placed in a third configuration in which the shutter is set to occlude the duct while keeping the intermediate hole substantially open, so as to prevent a fluid injected into the duct through the auxiliary opening from passing through the intermediate hole. In this condition, it is consequently possible to perform a unidirectional perfusion in which a fluid is injected into a blood vessel through the first opening of the tubular body of the cannula. In addition, part of the fluid flowing into the cavity of the tubular body flows at least in part into the duct, from which it exits through the intermediate hole. Providing a pressure transducer connected to the intermediate hole makes it possible to measure the pressure of the fluid injected into the blood vessel through the first opening in the cannula.

The valve device can furthermore be placed in a fourth configuration in which the shutter is set to occlude both the intermediate hole and the duct, so as to prevent a fluid injected into the duct through the auxiliary opening from reaching the first end of the duct and exiting through the intermediate hole.

According to a feature of the invention, the cavity of the tubular body defines a second opening in the cannula, preferably in the proximal portion of the tubular body, for the injection of a fluid into this cavity. The aforementioned fluid is intended to exit the cannula through the first opening and the auxiliary opening when the valve device is in the second configuration.

The proximal portion can be provided with a tubular connector at the second opening in order to connect the cannula to a fluid source, for example, through a tubular element.

According to a feature of the invention, the first end of the duct is placed in fluid communication with the cavity at the proximal portion of the tubular body. This technical solution proves particularly advantageous in promoting the injection into the duct of a portion of the fluid flowing into the cavity toward the first opening.

According to a feature of the invention, the duct is provided with the valve device in a portion which extends outside the tubular body, preferably in such a way as to be placed outside the body of the patient on whom the cannula is being placed in a blood vessel.

This feature is particularly advantageous in helping the physician to use the cannula according to the first, second, or third operating procedure.

According to a feature of the invention, the second end of the duct extends inside the tubular body, in particular inside the cavity. In this case, the second end of the duct ends at the tubular body so that the auxiliary opening defines a passageway in the connection portion. Preferably, the auxiliary opening of the duct coincides with the aforementioned passageway of the connection portion.

This feature is particularly suitable for making the cannula more compact, by avoiding the presence of components outside the tubular body in the connection portion which, let us recall, is intended to be placed inside a blood vessel.

According to a feature of the invention, the connection portion is without an opening arranged to allow a fluid to exit the cavity in the second direction. In other words, there is a wall that prevents the flow of fluid exiting the cavity in the second direction.

The duct is therefore the only passageway of the cannula that allows a fluid injected into the tubular body to exit in a direction opposite the first direction, that is, opposite the insertion direction of the cannula into the blood vessel. In addition, this solution prevents the blood introduced into the cannula through the first opening from exiting the cannula in the second direction.

This ensures full control over bi-directional perfusion of a fluid in a blood vessel by the user of the cannula.

According to a feature of the invention, the distal and proximal portions are substantially straight. The distal and proximal portions lie along x and y axes, respectively, which form an angle of preferably between 80° and 150°.

This feature is particularly suitable for promoting insertion of the cannula into the blood vessel while keeping the valve device far enough from the patient's body.

According to a feature of the invention, the distal portion comprises a free end having a shape tapering toward the first opening. This facilitates insertion of the distal portion into the blood vessel.

The proximal portion, however, may have a cross-section that widens toward a corresponding free end provided with the second opening.

According to a feature of the invention, the tubular body and the duct are made of a biocompatible plastic material.

According to a feature of the invention, the duct and/or tubular body are transparent.

This feature allows the user of the cannula to visually observe blood rising in the duct which, as mentioned earlier, indicates correct positioning of the cannula in the blood vessel.

In FIG. 1, number 100 refers to a cannula as a whole for fluid perfusion according to the invention, as a whole. The cannula 100 comprises a tubular body 1 extending from its proximal portion 2 to its distal portion 3.

The distal and proximal portions 2 and 3 are substantially straight and lie along respective axes X and Y, which form a convex angle α of 120°.

The tubular body 1 comprises a connection portion 4 lying between the proximal portion 2 and distal portion 3. The connection portion 4 is configured so as to follow a curve and is sized so as to be inserted into a blood vessel 17 through the distal portion 3.

The inside of the tubular body 1 is provided with a cavity 5 defining a first opening 6 in the distal portion 3. The first opening 6 allows a fluid to exit the cavity 5 in a first direction D1. In particular, the distal portion 3 comprises a free end 16 having a tapered shape in the direction of the first opening 6.

The cavity 5 furthermore defines a second opening 7 in the proximal portion 2 of the tubular body 1 for the injection of a fluid into the cavity 5.

With reference to the figures, the proximal portion 2 is provided with a tubular connector 13 at the second opening 7 in order to connect the cannula 100 to a fluid source, for example, through a tubular element.

The cannula 100 also comprises a duct 8 extending from its first end 9 to its second end 10. The first end 9 of the duct 8 is placed in fluid communication with the cavity 5 of the tubular body 1 so that a fluid flowing in said cavity 5 toward first opening 6 flows at least in part into the duct 8.

With reference to the figures, the first end 9 of the duct 8 is placed in fluid communication with the cavity 5 at the proximal portion 2 of the tubular body 1.

The second end 10 of the duct 8 is provided with an auxiliary opening 11 placed in the connection portion 4 of the tubular body 1 so as to allow a fluid to exit the duct 8 in a second direction D2 opposite to the first direction D1.

The duct 8 is provided with a valve device 12 designed to shut off, or allow, the flow of a fluid flowing through the duct 8 from one end to the other thereof 9, 10, depending on whether the valve device 12 is in a first configuration or a second configuration, respectively.

A fluid injected into the cavity 5 through the second opening 7 is therefore intended to exit the cannula 100 through the first opening 6 and through the auxiliary opening 11, if the valve device 12 is in the second configuration.

With reference to the figures, the valve device 12 is a three-way valve that can be moved between the first and the second configurations. The valve device 12 is provided with a knob 15 which, when rotated, is used to set the configuration of the valve device 12. A connector 14 extends from an intermediate hole 18 placed between the first and second ends 9, 10, of the duct 8.

Figure 3A:
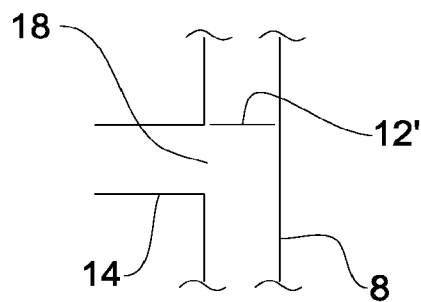
FIGS. 3A-3D are schematic drawings of a section of a duct of the cannula according to the invention, with a valve device in various configurations.
Figure 3B:
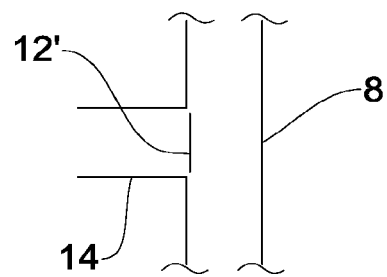

FIGS. 3A and 3B show the valve device 12 in the first and second configurations, respectively.

With reference to FIG. 3A, the valve device 12, when the first configuration, shuts off the duct 8 with the shutter 12' so as to divert a fluid injected into the duct 8 through the auxiliary opening 11 toward the intermediate hole 18, through which it flows into the duct 8.

With reference to FIG. 3B, the valve device 12, when in the second configuration, shuts off the intermediate hole 18 with the shutter 12', leaving the duct 8 open so that a fluid injected into the duct 8 through the first end 9 flows into the duct 8 until it reaches the second end 10, from which it exits through the auxiliary opening 11.

Figure 3C:
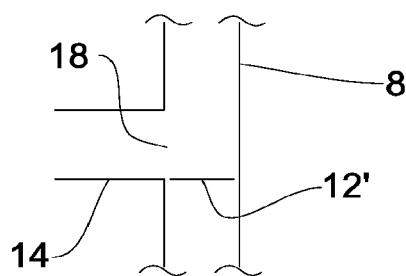
Figure 3D:
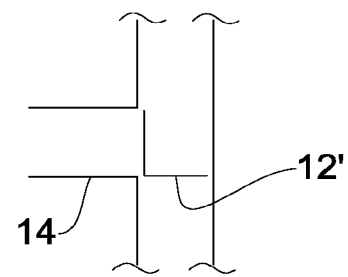

FIGS. 3C and 3D show the valve device 12 in a third and fourth configuration, respectively.

With reference to FIG. 3C, the valve device, when in the third configuration, shuts off the duct 8 leaving the intermediate hole 18 open, thus making it possible to measure the pressure of the fluid injected into the duct 8 through the first end 9 by a pressure transducer connected to the intermediate hole 18.

In reference to FIG. 3D, the valve device, when in the fourth configuration, shuts off both the intermediate hole 18 and the duct 8, thus preventing a fluid injected into the duct 8 through the auxiliary opening 11 from reaching the first end 9 of the duct 8 and passing through the intermediate hole 18.

Figure 2:
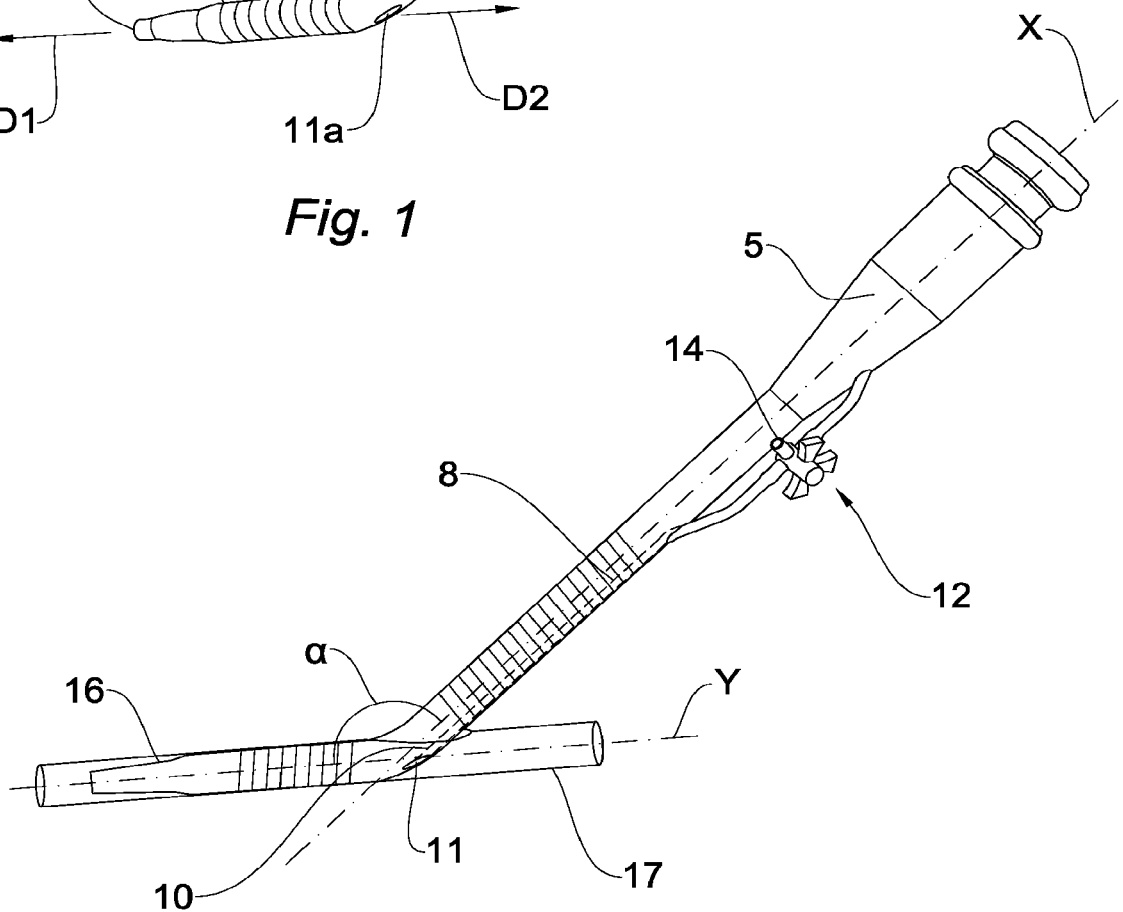
FIG. 2 shows the cannula of FIG. 1 partially inserted into a blood vessel.

With reference to FIGS. 1 and 2, the duct 8 is provided with the valve device 12 in a portion lying outside the tubular body 1, so as to be located outside the body of the patient on whom the cannula 100 is being placed in a blood vessel, while the second end 10 of the duct 8 lies inside the cavity 5. In particular, the aforementioned second end 10 ends on the tubular body 1 in such a way that the auxiliary opening 11 defines a passageway 11a in the connection portion 4.

Specifically, the auxiliary opening 11 of the duct 8 coincides with the aforementioned passageway 11a of the connection portion 4. In reference to the figures, the connection portion 4 is without an opening arranged to allow a fluid to exit the cavity 5 in the second direction D2. In other words, there is a wall that prevents the flow of fluid exiting the cavity in the second direction.

The tubular body 1 and duct 8 are made of a biocompatible plastic material.

In addition, the aforementioned items 1 and 8 are transparent to facilitate the visibility of blood or, more generally, a fluid in the duct 8 and cavity 5.

The invention therefore solves the stated problem while achieving a number of benefits. In particular, the cannula according to the invention is particularly versatile, as it allows for both unidirectional and bi-directional perfusion.

The invention claimed is:

1. A cannula for fluid perfusion comprising:
   a tubular body extending from a proximal portion to a distal portion thereof, the tubular body being provided internally with a cavity defining a first opening in the distal portion allowing a fluid to exit the cavity in a first direction,
   the tubular body comprising a connection portion lying between the proximal and distal portions, the connection portion being configured or configurable so as to have a curved shape and being sized so as to be inserted into a blood vessel by the distal portion,
   a duct extending from a first end to a second end thereof, the second end being provided with an auxiliary opening placed at the connection portion so as to allow a fluid to exit the duct in a second direction opposite to the first direction,
   wherein the first end is placed in fluid communication with the cavity so that a fluid flowing in the cavity toward the first opening flows at least in part into the duct, and the duct is provided with a valve device designed to shut off, or allow, the flow of a fluid flowing through the duct from one end to the other thereof, depending on whether the valve device is in a first configuration or in a second configuration, respectively,
   wherein the first end of the duct is placed in fluid communication with the cavity at the proximal portion of the tubular body, and
   wherein the duct is provided with an intermediate hole located between the first end and the second end, and the valve device is a three-way valve comprising a shutter arranged inside the duct, the shutter, when in the first configuration, being designed to occlude the duct while keeping the intermediate hole open so as to divert a fluid injected into the duct through the auxiliary opening toward the intermediate hole, and when in the second configuration, being designed to occlude the intermediate hole while keeping the duct open so as to allow a fluid to flow from the first end to the second end, or vice versa.

2. The cannula according to claim 1, wherein the second end of the duct lies inside the tubular body in such a way that the auxiliary opening defines a passageway in the connection portion.

3. The cannula according to claim 1, wherein a connector extends from the intermediate hole and is arranged to be connected to an inlet tube of a pressure transducer.

4. The cannula according to claim 1, wherein the valve device is placed at a portion extending outside the tubular body.

5. The cannula according to claim 1, wherein the cavity defines a second opening in the proximal portion for injecting a fluid intended to exit the cannula through the first opening and through the auxiliary opening, if the valve device is in the second configuration.

6. The cannula according to claim 1, wherein the connection portion has a wall that prevents fluid from flowing out of the cavity in the second direction.

7. The cannula according to claim 1, wherein the distal portion and the proximal portion are substantially straight, lying along respective axes forming an angle of between 80° and 150°.

8. The cannula according to claim 1, wherein the distal portion comprises a free end having a shape tapering toward the first opening.

9. The cannula according to claim 1, wherein the tubular body and the duct are made of biocompatible plastic material.

10. The cannula according to claim 1, wherein the duct is transparent.

* * * * *